United States Patent [19]

Kilejian

[11] 4,373,530

[45] Feb. 15, 1983

[54] SURGICAL STITCHING INSTRUMENT

[75] Inventor: Vahe Kilejian, Fresno, Calif.

[73] Assignee: Lisa Ann Kilejian, Central Point, Oreg.

[21] Appl. No.: 278,980

[22] Filed: Jun. 29, 1981

Related U.S. Application Data

[63] Continuation-in-part of Ser. No. 137,391, Apr. 4, 1980, abandoned.

[51] Int. Cl.³ .............................................. A61B 17/04
[52] U.S. Cl. ................................. 128/334 R; 128/340
[58] Field of Search ................ 128/326, 334 R, 335.5, 128/339, 340

[56] References Cited

U.S. PATENT DOCUMENTS

| | | | |
|---|---|---|---|
| 1,635,066 | 7/1927 | Wells | 128/334 R |
| 1,822,330 | 9/1931 | Ainslie | 128/340 |
| 2,286,578 | 6/1942 | Sauter | 128/334 R |
| 3,033,204 | 5/1962 | Wood | 128/326 |

FOREIGN PATENT DOCUMENTS 263865  11/1927  Italy ................................ 128/334 R Primary Examiner—Stephen C. Pellegrino
Attorney, Agent, or Firm—Huebner & Worrel

[57] ABSTRACT

A surgical stitching instrument of forceps-like construction having a pair of arms pivotally interconnected for movement about an axis and respectively terminating in a suture holder which has a needle receiving slot and notches on opposite sides of the slot adapted to receive a suture disposed across the slot and in a needle which has a point, an inner edge, an outer edge divergent from the inner edge away from the point, and a hook spaced from the point of the needle, the needle being movable through a tissue to be stitched from a position retracted from the slot into a position in the slot while camming the suture out of the notches to a position disposed for snagged engagement by the hook so as to be dragged through the tissue as the needle is subsequently returned to the retracted position, the invention being characterized by the hook having an outer slot providing an inner end and being disposed substantially radially of the axis and an inner slot continuous with the inner end of the outer slot extended substantially tangentially of the axis from the inner end whereby such a suture can be tensioned by drawing the needle endwardly of its arm.

9 Claims, 13 Drawing Figures

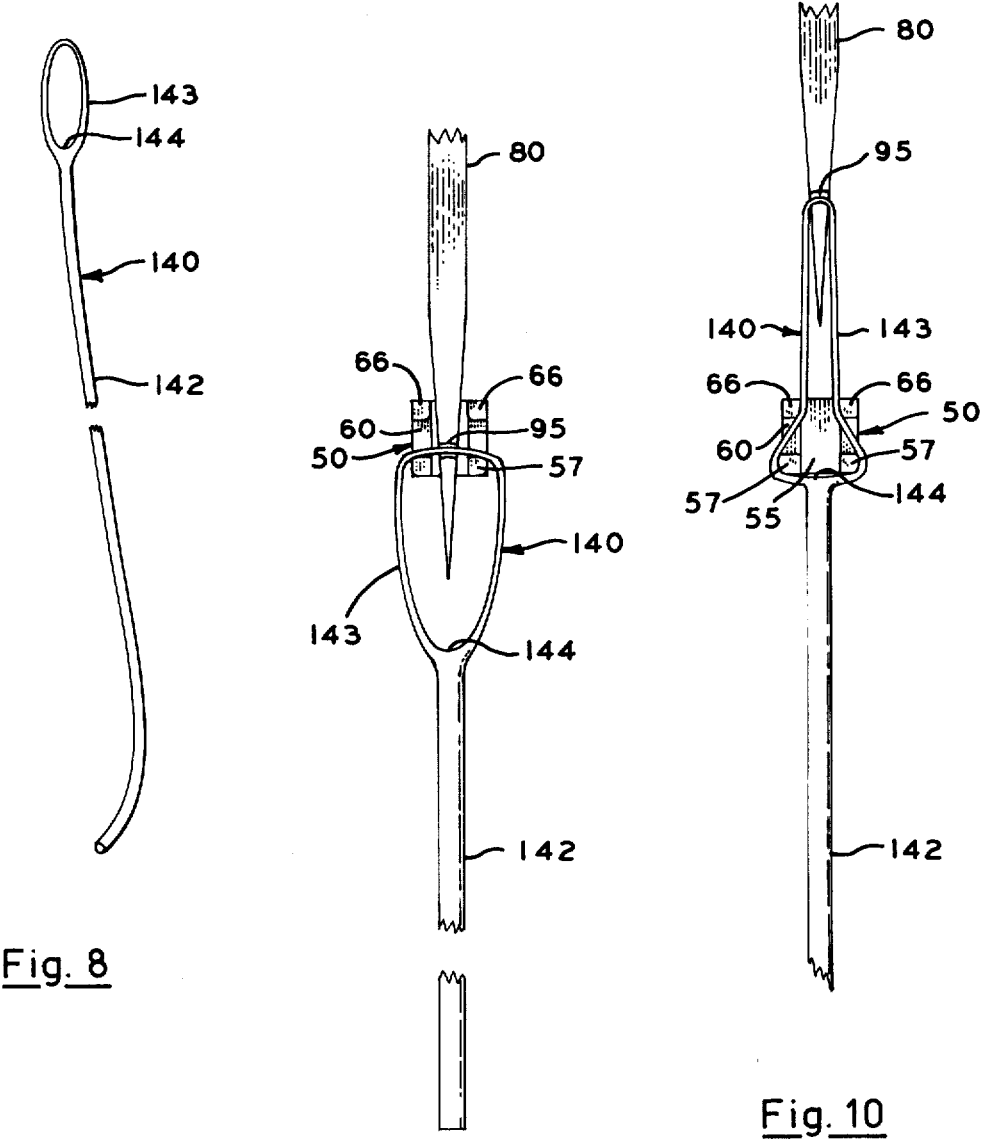

SURGICAL STITCHING INSTRUMENT

RELATED APPLICATION

This application is a continuation-in-part of U.S. patent application Ser. No. 137,391 filed Apr. 4, 1980 entitled "Surgical Stitching Instrument", now abandoned.

BACKGROUND OF THE INVENTION

1. Field of the Invention

The present invention relates to a surgical stitching instrument providing a combined suture holder and needle in which the needle is adapted to pierce tissue to be stitched, pick up a suture from the holder after piercing the tissue, and to retract through the tissue while dragging the suture from the holder therethrough and more particularly to such an instrument which is manipulatable with one hand by a surgeon while freeing the other hand for tissue arranging, positioning or other ancillary functions particularly desirable in deep surgery. The needle is attached to and is an integral part of the instrument, thus allowing better contact of the needle and ease of manipulation through tissues even in blind stitching.

2. Description of the Prior Art

It is a well-known surgical practice to clamp a needle with its attached suture with a needle holder and to push the needle through tissues to be stitched until it exits at the opposite side of the tissue. The needle is then released and clamped again at its leading end and extracted through the tissue together with the attached suture. This procedure is satisfactory in many instances except in suturing deep structures, in the presence of bleeding or exudation, it is difficult to reapply the needle holder after the needle has pierced the tissue.

Another well-known method of suturing, especially in deep surgery, is with the use of a Boomerang needle holder. The suture is clamped with a specialized instrument manipulated by one hand, the instrument then being maneuvered to place the suture adjacent to the tissue. A needle having a hook adjacent to the point thereof is then manipulated with another specialized instrument held in the other hand to pierce the tissue and the clamping instrument maneuvered so that the hook snags the suture. The suture is then unclamped with the one hand and the needle is withdrawn along its insertion path with the other hand to draw the suture through the tissue. The instruments and needle are then put aside and the suture tied.

This procedure is disadvantageous for several reasons. Both hands are fully employed during the insertion of the suture since one hand is required to operate the needle manipulating instrument while the other hand is required to operate the suture clamping instrument. It has long been recognized that it would be highly advantageous for surgeons to have one hand free for other procedures during such stitching operations.

These conventional procedures are relatively slow since, in sequence, the suture must be clamped, the needle must be guided through the tissue, the suture clamping instrument and the needle manipulating instrument must be operated to engage the suture with the needle, and the instruments must be withdrawn without disengaging the suture so as to draw the suture through the tissue.

The needle grasping and the suture clamping instruments are both of specialized construction, require great dexterity for proper operation, and the needle manipulating instruments are frequently complicated in structure and mode of operation.

It has also long been recognized that it would be highly advantageous to provide a single instrument usable by one hand whereby simple opening and closing movements pass a suture through a tissue in deep surgery and dispose the suture for tying.

PRIOR ART STATEMENT

In conformance with 37 C.F.R. §1.97 and §1.98, the applicant states that he is not aware of any prior art other than that discussed above that is relevant to the patentability of the subject invention and the references cited against the above identified parent application, copies of which are attached, as follows:

Wells—U.S. Pat. No. 1,635,006—July 5, 1927
Ainslie—U.S. Pat. No. 1,822,330—Sept. 8, 1931
Sauter—U.S. Pat. No. 2,286,578—June 16, 1942
Wood—U.S. Pat. No. 3,033,204—May 8, 1962
Tonnini (Italian) Pat. No. 263,865—Nov. 12, 1927

SUMMARY OF THE INVENTION

It is an object of the present invention to provide an improved surgical stitching instrument and suture.

Another object is to provide such an instrument adapted to be manipulated by one hand, while the other hand is free for any other desired simultaneous procedure.

Another object is to provide such an instrument having a needle which pierces a tissue, picks up a suture held by the instrument, and draws the suture through the tissue by sequential opposite movements of a pair of handles held by one hand.

Another object is to provide an instrument which is operable rapidly and conveniently to pass a suture through a tissue.

Another object is to provide such an instrument which facilitates the placing of sutures in deep surgery.

Another object is to provide a surgical stitching instrument suited to suture placement in blind surgery.

Another object is to provide a surgical stitching instrument which can be manipulated to tension a suture implanted thereby in a maximum of relative directions from the instrument and particularly outwardly in substantial alignment with the handles.

A further object is to provide improved elements and dispositions thereof in a surgical stitching apparatus which is simple in construction, durable, and fully effective in accomplishing its intended purpose.

BRIEF DESCRIPTION OF THE DRAWINGS

FIG. 8 is a plan view of a looped suture having particular utility with the surgical stitching instrument of the present invention.

FIG. 9 is a schematic top view of the looped suture, a needle, and a holder of the present invention in relatively contracted positions for the needle to pick up the suture.

FIG. 10 is a schematic top view of the suture, needle, and holder somewhat similar to FIG. 9 but with the needle and holder in relatively retracted positions as assumed to draw the suture through tissue to be stitched.

DESCRIPTION OF THE PREFERRED EMBODIMENT

Figure 2:
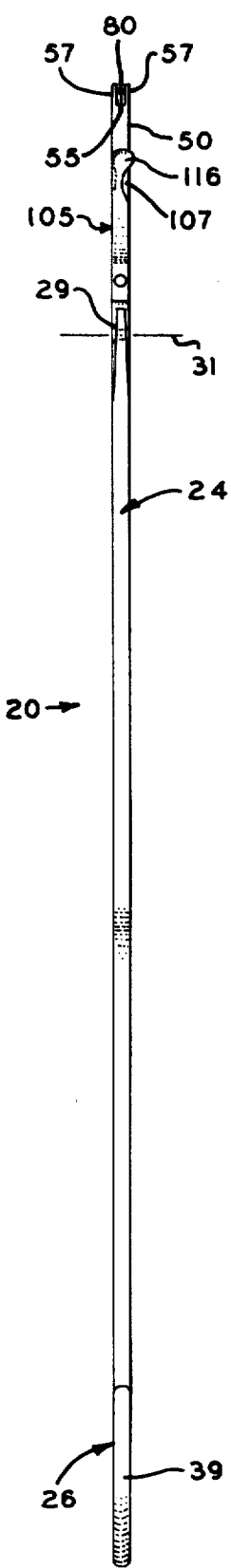
FIG. 2 is an edge view of the instrument of FIG. 1.
Figure 1:
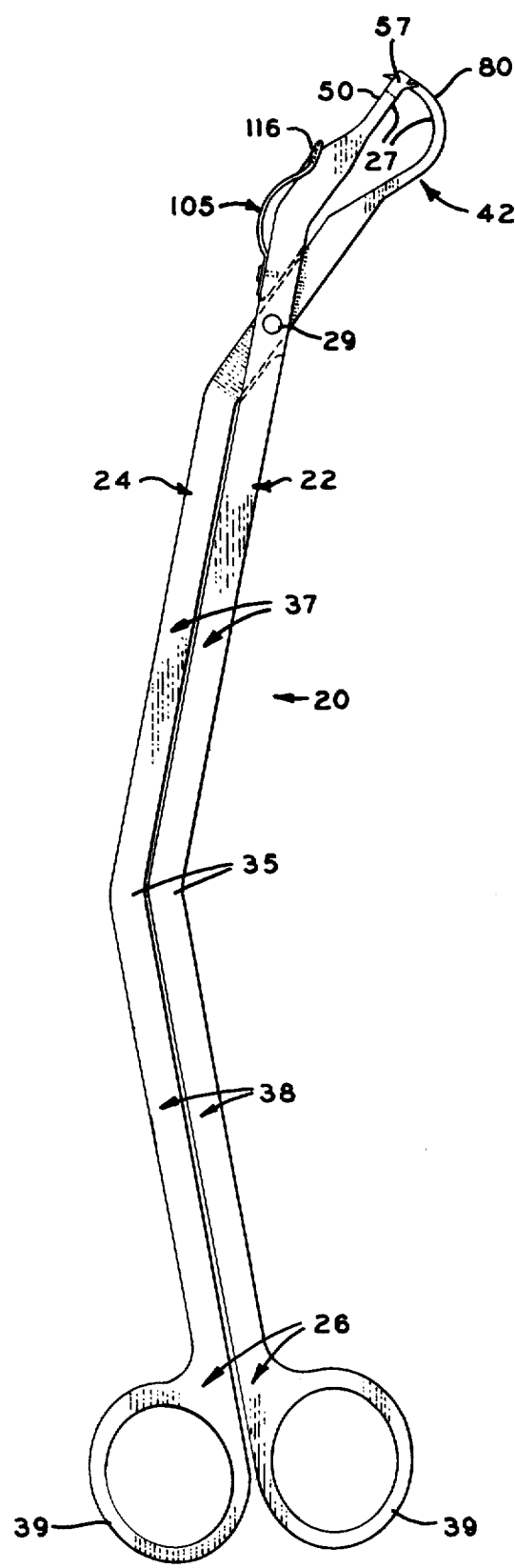
FIG. 1 is a side view of a surgical stitching instrument embodying the principles of the present invention.

Referring more particularly to the drawings, in FIGS. 1 and 2, there is shown a surgical stitching instrument 20 embodying the principles of the present invention with a pair of juxtapositioned tissues 21 to be stitched by the instrument. The instrument is a forceps having a first arm 22 and a second arm 24. Each arm has a gripping end 26 and an opposite sewing tip 27. The arms are interconnected by a pin 29 for pivotal movement about an axis 31 which is disposed substantially closer to the sewing tips than to the gripping ends.

The portions of the arms 22 and 24 between the pin 29 and the gripping ends 26 are generally parallel and for deep surgical procedures, each preferably has a central bend 35. The bend thus defines a pair of parallel sections 37 individual to the arms between the pin and the bend and a pair of parallel sections 38 outwardly of the bend. The bend is of a form well known in surgical instruments to facilitate manipulation of the instrument without impairing the visibility of the sewing tips 27. The gripping ends are provided with individually oppositely extended finger loops 39 of conventional configuration. The arms cross at the pin so that manipulating the gripping ends to move them apart moves the sewing tips from each other to spaced retracted positions 41 shown in FIGS. 3 and 4, while moving these ends toward each other moves the sewing tips toward each other into closed positions 42 shown in FIG. 1 and in dash lines in FIG. 3. These positions are spaced from each other a distance such that in the retracted positions 41, a tissue 21 to be stitched can be received between the sewing tips.

The arms 22 and 24 are bent in the vicinity of the pin 29 into a configuration such that the sewing tips 27 extend generally parallel to each other from the pin in the same direction from the sections 37 as the sections 38 extend. Since the arms are interconnected for pivotal movement about the axis 31, the sewing tips are constrained to move in concentric arcs between their retracted positions and their closed positions. The arms are configured so that these arcs lie substantially in a common plane normal to the axis.

Figure 3:
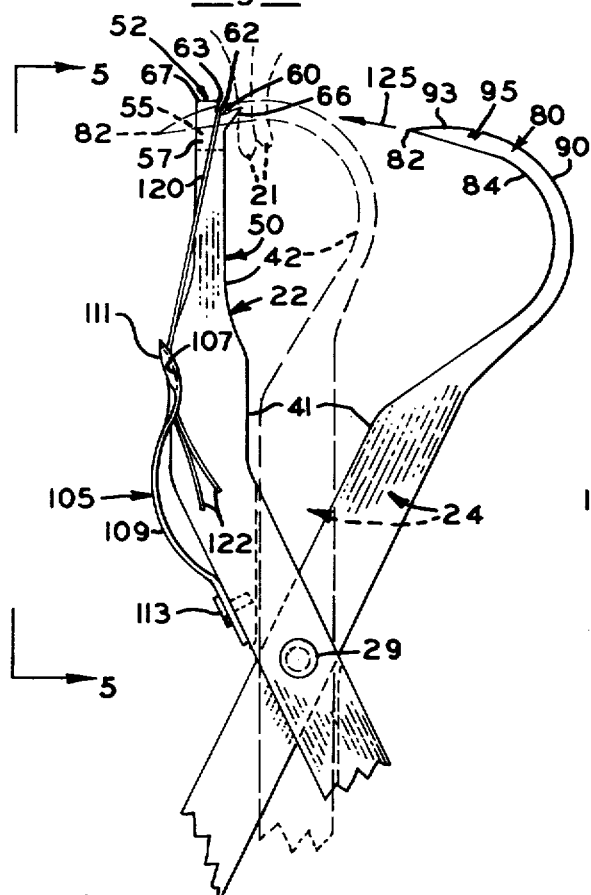
FIG. 3 is a somewhat enlarged fragmentary side view of a needle, suture and holder of the instrument together with a tissue to be stitched shown in dashed line, the needle being shown in retracted position in full line and in contracted position in dashed line as sequentially positioned during operation to pierce the tissue and pick up the suture.
Figure 5:
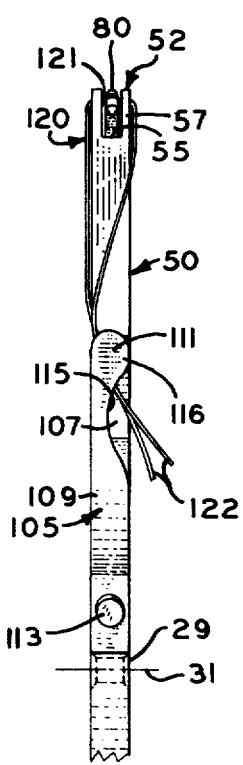
FIG. 5 is a fragmentary edge view taken from the position of line 5—5 of FIG. 3.

The sewing tip 27 of the first arm 22 constitutes a suture holder 50 disposed remotely from the pin 29 and best shown in FIGS. 3 and 5. The holder is depicted as being unitarily constructed with the balance of the arm. However, if desired, the holder can be releasably mounted in any manner which is satisfactory for use with surgical instruments. The holder terminates oppositely of the axis in an end 52 which is generally planar and normal to a radius from the axis 31. Viewed along such a radius, the end is of generally rectangular configuration, typically having a length of 6 mm along the common plane of movement and a width of 5 mm in a direction parallel to the axis. The holder has a slot 55 extending through it longitudinally of the end along this plane. The slot opens through the end and, typically, is 1.5 mm wide and 5 mm deep. The holder is divided by the slot into a pair of sides 57 extended parallel to the slot.

The sides 57 of the suture holder 50 are provided with individual notches 60. The notches are thus disposed oppositely of the slot 55 as viewed in the direction parallel to the axis 31 and are aligned with each other in such a direction. Each notch has an inner closed end 62 disposed toward the axis and an opposite outer opening end 63. Each notch divides the corresponding side of the holder into a first leg 66 and a second leg 67. The first leg is disposed in a direction toward the first arm 22 from the notch, and the second portion is disposed oppositely of the notch from the first arm. These legs are thus disposed from each other in a direction parallel to the plane of movement of the sewing tips with the first leg being disposed in the direction of movement of the tip of the second arm 24 from its closed position 42 toward its retracted position 41. Typically, the second legs have a length of 2 mm along this direction, the notch is approximately 1 mm in width, and the first legs extend to a point spaced 4 mm from the second legs. Each notch extends approximately at a 45° angle from its open end toward its closed end in a direction away from the corresponding first leg. The outer ends are, therefore, disposed from the inner closed ends in the direction of movement from the closed position to the retracted position.

Figure 4:
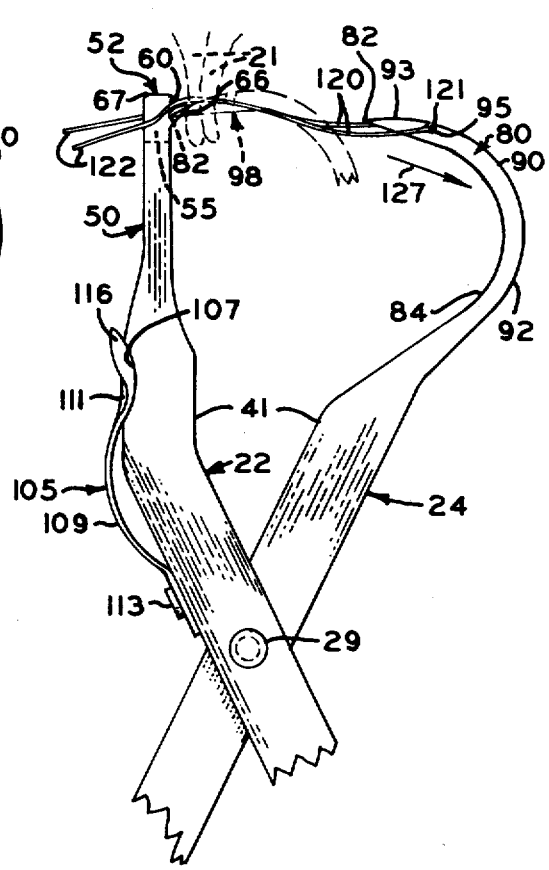
FIG. 4 is a view similar to FIG. 3 depicting the instrument in a further operating position with the needle shown in dashed line immediately after it has picked up the suture and in full line retracted to pull the suture through the tissue.

As best shown in FIGS. 3 and 4, the first legs 66 have a spur-like configuration extended toward the second arm 24 in a direction away from the corresponding notch 60. The first legs extend a lesser distance in the direction outwardly of the slot 55 and along a radius from the axis 31 than the second legs extend in this direction. The first leg, typically, terminates 1.5 mm closer to the axis than does the second leg.

Figure 6:
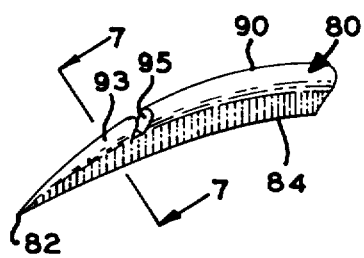
FIG. 6 is a fragmentary perspective view at a further enlarged scale of a distal portion of the needle.
Figure 7:
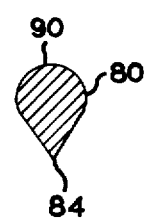
FIG. 7 is a section of the needle at a still further enlarged scale taken on line 7—7 of FIG. 6.

The sewing tip 27 of the second arm 24 remotely of the pin 29 constitutes a tissue-piercing, sickle-shaped needle 80, best shown in FIGS. 4, 6, and 7. As shown, the needle is unitarily constructed with the arm, but may be releasably mounted thereon in any suitable manner. The needle has a sharpened point 82 which is disposed toward the holder 50 when the sewing tips are in their retracted positions. The point is spaced radially from the axis 31 a distance less than the spacing of the notches from the axis. In the closed position, the hook 95 of the needle 80 should be at a slightly more distal position than the notch 60 of the suture holder 50. In other words, the radius of the hook 95 from the pin 29, should be slightly (0.5 to 1 mm) longer than the radius of the notch 60 from the pin. The needle has an arcuate, sharpened inner edge 84 disposed toward the axis and concentric therewith which facilitates tissue penetration. The radius of the inner edge is approximately the radius from the axis to the closed ends 62 of the notches 60, and the needle lies substantially in a plane through the slot normal to the axis. The needle is disposed in relation to the balance of the second arm so that the needle extends through the slot 55 when the tips are in their closed or contracted positions. In the contracted positions, the point of the needle protrudes 3 mm to 4 mm from the holder in the direction of movement of the needle toward the contracted position. In connection with the inner edge, it will be noted that when the needle is extended through the slot, the ends of the first legs 66 of the sides 57 of the suture holder are spaced closer to the inner edge than are the ends of the second legs 67.

The needle 80 has an outer edge 90 disposed oppositely of the inner edge 84. The outer edge is arcuate, having a base portion 92 which is generally parallel to the inner edge 84 and spaced farther from the axis than the notches 60. The outer edge has a distal portion 93 which is arcuately convergent with the inner edge to the point 82. This distal portion extends from the point 82 of the needle to a hook 95 formed by a notch in the outer edge. The hook is open in a direction away from the axis. As best shown in FIG. 7, the distal portion is blunt to avoid inadvertently cutting the tissue 21 outwardly thereof. As shown in FIG. 3, the hook is spaced from the point such that the hook is aligned with the notches 60 in the suture holder 50 when the sewing tips 27 are in their closed positions 42. This hook is spaced approximately 6 mm from the point when the holder is constructed in accordance with the previously stated typical dimensions. The point of the needle thus extends beyond the holder when the tips are in their closed positions and the needle passes through a position 98, shown in FIG. 4, in which the point is disposed in the slot 55 as the needle moves between the retracted and closed positions. The hook extends at an angle to a radius from the axis, the open end of the hook being disposed from its closed end in the direction in which the needle moves from its closed position toward the retracted position 41.

The instrument is provided with a clip 105, best shown in FIGS. 4 and 5, mounted on the suture holder 50 for movement with it. The clip is associated with a relatively shallow arcuate depression 107 in the holder on the side thereof opposite to the second arm 24. The depression is disposed approximately midway between the end 52 of the holder and the pin 29 and is thus spaced from the slot 55 and the notches 60 in a direction toward the axis 31. The clip includes an elongated arm 109 of resilient material extending longitudinally in a direction parallel to the holder. The arm has a flared longitudinal end portion 111 disposed in the depression and an opposite end portion spaced toward the joint from the depression and fixedly secured to the holder by a rivet 113 or any other suitable means. The arm is return bent between these ends so that the flared end is resiliently urged into engagement with the depression. One of the longitudinal sides of the arm has a notch 115 adjacent to the flared end portion. The flared portion is rounded and has a wing 116 extended outwardly of the holder adjacent to the notch. The edge of this end portion about the wing is curved away from the suture holder.

In FIGS. 8, 9, and 10, a looped suture 140 is illustrated, which, in combination with the surgical stitching instrument 20, facilitates difficult to reach or deep or blind surgery. For example, operations to correct female incontinence have heretofore constituted major surgery. Relatively large openings have been required to make possible the proper placement of sutures particularly where bleeding or exudation is encountered. The stitching instrument of the present invention, particularly when utilized with the looped suture 140, has made possible the effective performance of such surgery and similar surgical procedures through small openings in the abdomen, obviating major surgery in such instances.

The suture 140 is made of any suitable material and consists of a flexible strand 142 of any desired caliber having a loop 143 at an end thereof which is joined with the strand by a throat or juncture 144. To minimize the magnitude of the perforations required in the tissue 21, the strand is preferably at least about the caliber or diameter of the throat, and at least about twice the caliber of each filament of the loop. The throat may be formed in any suitable manner, as by bending, weaving, clamping, or the like.

In many instances, it is desirable to tension the suture by moving the instrument and the free ends of the suture relatively away from each other while the suture is still engaged in the hook 95. For example, as shown in FIG. 4, the suture 120 can be tensioned by moving the needle in the direction of its retraction from the holder 50 while holding or anchoring the suture. However, if the instrument is moved endwardly in the direction of the gripping ends 26 to tension the suture in endward extension from the sewing tips 27, the suture disengages from the hook 95. A similar unsatisfactory result ensues if the needle is moved toward contracted position while the suture is extended oppositely from the hook. A second form of needle of the present invention permits the instrument to be manipulated so as to tension the suture in virtually every direction from the needle without inadvertently disengaging the hook.

SECOND FORM OF NEEDLE

Figure 12:
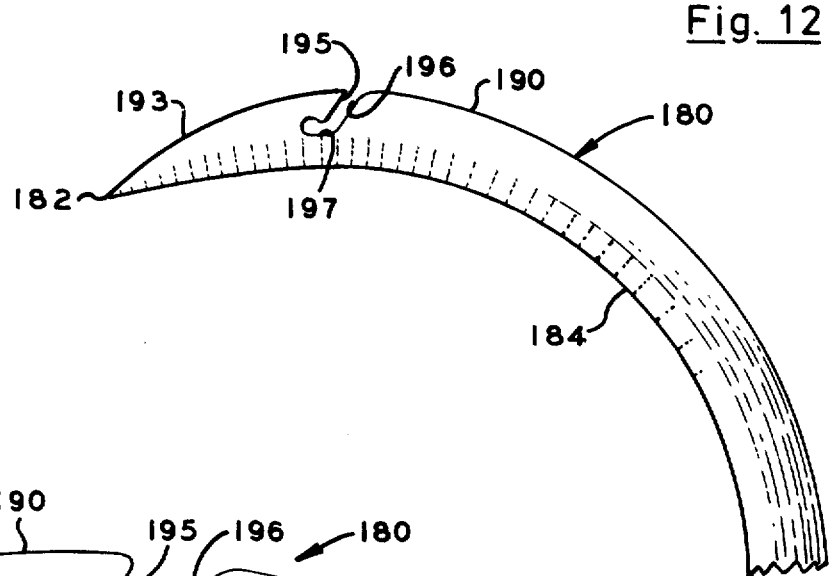
FIG. 12 is an enlarged fragmentary side elevation of the needle of FIG. 11.
Figure 13:
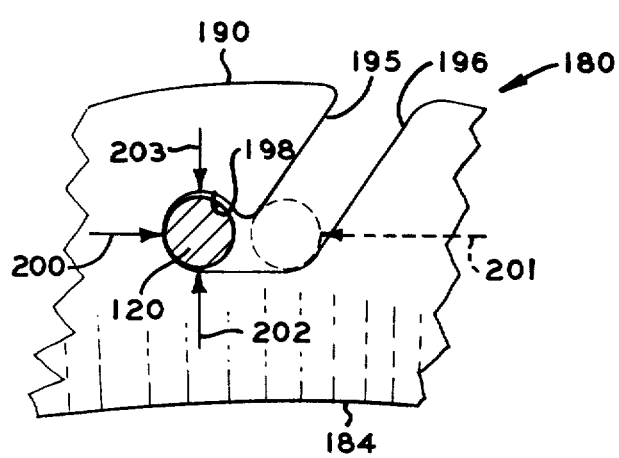
FIG. 13 is a further enlarged fragmentary side elevation of the needle of FIGS. 11 and 12.
Figure 11:
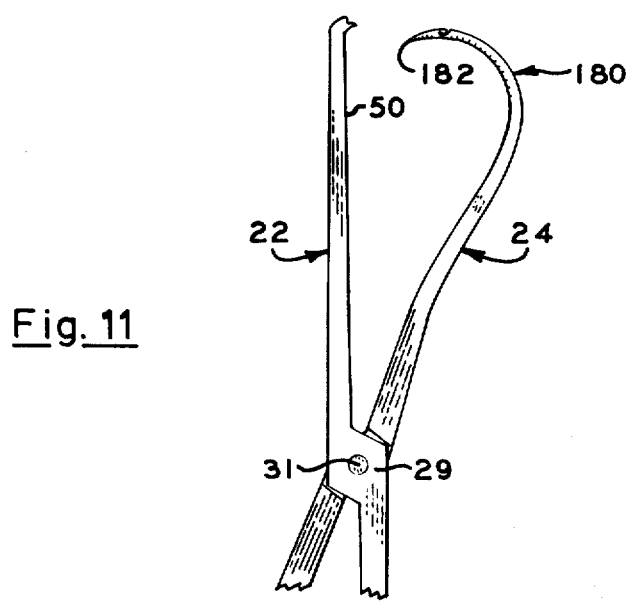
FIG. 11 is a fragmentary side elevation of a surgical stitching instrument embodying the principles of the present invention and employing a second form of needle.

Referring to FIGS. 11 through 13, a second form of needle is shown at 180. It is provided as an integral part of the second arm 24, as described for the needle 80, and has the same association with the holder 50 as previously described. It has a point 182, a sharpened inner edge 184, a blunt outer edge 190, and a distal camming surface 193. Spaced from the point, the outer edge has a hook 195 of generally "J" shape. The hook has an outer slot 196 which extends inwardly from the outer edge 190 obliquely of a radius of the axis 31 and having an inner end 197. The angle between the outer slot and the radius from the axis is preferably approximately 35°. Thus, the angle between the outer slot and a tangent of the axis is approximately 55°. From the inner end of the outer slot an inner slot 198 extends toward the point and slightly outwardly so as to form a pocket at the inner end of the outer slot. The angle between the inner slot and a tangent to the axis also is not critical but preferably is several degrees. As will subsequently become apparent, the J-shaped hook makes possible the tensioning of the suture in virtually all directions desired.

OPERATION

The operation of the described embodiments of the present invention is believed to be clearly apparent and is briefly summarized at this point. The instrument 20 is for use with a conventional suture 120, shown in FIGS.

3, 4, and 5, having a central portion 121 and opposite end portions 122. Initially, as shown in FIGS. 1 and 3, the instrument is disposed with the tips 27 in their retracted positions 41 by grasping the ends 26 and moving these ends apart. Grasping of the gripping ends during this manipulation is facilitated by the loops 39. The suture is then mounted on the instrument with the central portion received in the notches 60 and extended transversely across the slot 55 in bridging relation thereto and in spaced relation to the axis 31.

With the central portion 121 of the suture 120 so received in the notches 60, the end portions 122 are placed together and inserted between the flared end portion 111 of the clip 105 and the depression 107 in the suture holder 50 as shown in FIGS. 3 and 5. This insertion is facilitated by the wing 116 and turned up edge of the flared portion which guide the suture into the depression. The end portions of the suture are frictionally engaged between the arm due to the resiliency of the arm so that the suture is held in a taut condition where it bridges the slot 55.

With the instrument 20 grasped at the gripping ends 26 by one hand to maintain the tips 27 in their retracted positions 41, the instrument is manipulated with this hand to a position, best shown in FIG. 3, wherein the suture holder 50 and the needle 80 or 180 are disposed oppositely of the tissues 21 in which it is desired to emplace the suture. The gripping ends are then manipulated with the one hand to bring them together and to move the tips toward their closed positions 142 as indicated by the arrow 125 in FIG. 3. As the tips move toward their closed positions, the needle 80 or 180 pierces the tissues, this piercing being facilitated by the sharpened points 82 or 182 and inner edges 84 or 184. When the point of the needle emerges from the tissues, it moves into the position 98, shown in FIG. 4, in which the point is in the slot 55. As the needle continues to move, its outer edge 90 or 190 engages the central portion 121 of the suture 120 between the notches 60. Since the point of the needle is closer to the axis 31 than this portion of the suture, the point slides under the suture. With the point beneath the central portion, further movement of the needle toward the contracted position results in the outer edge of the needle along its distal portion 93 or 193 camming the suture outwardly of the notches. Since this outer edge along the distal portion is blunt, the suture is not injured by the needle during this camming action. As the needle attains its contracted position as shown in FIG. 3, the suture, which is held taut by the clip 105, is snagged by the hook 95 or 195 when the hook becomes aligned with the notches.

After the tips 27 have reached their closed positions 42, the gripping ends 26 are moved apart by the hand which has grasped these ends during the above-described piercing of the tissues 21 and snagging of the suture 120 by the hook 95 or 195. This movement, of course, causes the tips to move toward their retracted positions 41, as indicated by the arrow 127 in FIG. 4. As the needle moves from the closed position, the suture is dragged by the hook from the holder 50 through the pierced tissues. Since the notches 60 are angularly related to a radius from the axis 31 with their ends 63 disposed in the direction of this movement from their closed ends 62, the suture is drawn from the holder and moves with the needle. The similar angular disposition of the hook prevents the suture from becoming disengaged from the needle as the needle moves through the tissue into the retracted position. The needle thus draws the suture from its frictional engagement by the arm 109 to the extent as necessary to pass the suture through the tissues. When the needle is moved into its retracted position in relation to the holder, the suture is free to move from the notch so that the instrument 20 can be withdrawn and the suture disengaged from the clip 105 leaving the suture in the tissues. The instrument 20 can then be put aside and the suture tied.

It will be apparent that once the suture 120 is installed in the instrument 20, as shown in FIG. 3, only one hand is required to position the instrument in a desired relation to the tissues 21 and, by sequential movement of the gripping ends toward and from each other, to pierce the tissues and to drag the suture through them. The other hand is thus free to perform any other desired procedure during this sequence. This sequence of movements can be performed simply by sequentially closing and opening one hand. The suture holder 50 and the needle 80 are necessarily aligned to snag the suture 120 when the needle pierces the tissues, so that no maneuvering of the instrument is required other than that required to position the needle in relation to the tissues before performing this closing and opening movement. This limited maneuvering of the instrument is, of course, carried out without changing the grasp of the one hand on the gripping ends.

When unusually deep or difficult suturing is required, the instrument 20 preferably utilizes the looped suture 140 of FIGS. 8, 9, and 10. The loop 143 is preliminarily located in the notches 60 transversely of the slot 55 as shown in FIG. 9. As the ends 26 of the instrument are grasped, the needle 80 penetrates the tissue 21. After the needle penetrates the tissue 21, it passes under the portion of the loop 140 located in the notches until the hook 95 or 195 engages the loop. This condition is seen in FIG. 9.

As the needle 80 and holder 50 retract, as shown in FIG. 10, the opposite sides of the loop 143 are drawn tightly about the sides 57, securing the suture on the instrument. Under such conditions, the loop 143 of the suture can be tensioned between the needle 80 and holder 50 and precisely positioned. When desired, the loop can be slipped off the sides 57 and as much as desired of the strand 142 drawn through the tissue by manipulation of the instrument 20.

The specialized configuration of the J-shaped hook 195 enables the instrument 20 to be manipulated to tension the suture 120 in substantially all relative directions of extension therefrom. The hook 195 has an outer slot 196 extended inwardly from the outer edge 190 and an inner slot 198 continuous with the inner end 197 of the outer slot and extended forwardly and slightly outwardly with respect to the axis 31. The hook 195 is, of course, adapted to receive the suture 120 therein. The outer slot 196 is defined in part by a surface facing in the direction of retraction of the needle, to the right as viewed in FIGS. 12 and 13, which is engageable by the suture to tension the suture in the direction of such retraction of the needle upon movement of the needle relative to the tissues 21 in the direction of its retraction, as shown by the arrow 200 in FIG. 13. The outer slot 196 is also defined in part by a surface facing in the direction of contraction of the needle engageable by the suture to tension the suture in the direction of contraction of the needle, to the left as viewed in FIGS. 12 and 13, as shown by the arrow 201, upon movement of the needle relative to the tissue in the direction of its contraction. The inner slot 198 is defined in part by a surface facing outwardly of the axis 31 engageable by the suture to tension the suture radially outwardly of the axis upon movement of the needle radially outwardly relative to the tissue as shown by the arrow 202. The inner slot 198 is also defined in part by a surface facing inwardly of the axis 31 engageable by the suture to tension the suture radially inwardly of the axis upon movement of the needle radially inwardly relative to the tissue, as shown by the arrow 203.

It will be seen that the stitching instrument 20 is fully operable with one hand, thus freeing a surgeon's other hand for other use. It provides a needle 80 and 180 to pierce the tissue 21, a holder 50 which automatically presents a suture 120 or 140 in a position to be picked up by the needle, and a hook 95 and 195 on the needle to pull the suture through the pierced tissue as the needle withdraws through the tissue. The looped suture 140 when used with the instrument of the present invention 20 can be employed tightly to grasp the suture for dependable manipulation. The instrument is economical, durable, and fully effective in accomplishing its intended purposes.

Although the invention has been herein shown and described in what are conceived to be the most practical and preferred embodiments, it is recognized that departures may be made therefrom within the scope of the invention, which is not to be limited to the illustrative details disclosed.

Having described my invention, what I claim as new and desire to secure by Letters Patent is:

1. A surgical stitching instrument comprising:
   A. a suture holder having a needle receiving slot and aligned notches on opposite sides of the slot adapted to receive a suture therein disposed transversely of the slot, the notches being disposed in a common plane and having an outer open end and a closed inner end;
   B. a needle having a sharpened point, an inner edge, an outer edge divergent from the inner edge away from the point, and a hook in the outer edge spaced from the point; and
   C. means mounting the holder and needle for relative movement between a retracted position spaced to receive a tissue to be stitched therebetween and a contracted position with the point of the needle in the slot of the holder, the needle being adapted to pierce the tissue disposed therebetween as the needle moves from its retracted position toward the holder, the point being adapted to slide under such a suture in the notches of the holder in movement into the slot, the inner edge of the needle being sharpened to cut the suture in the notches of the holder during such movement of the needle into the slot, the outer edge having a camming surface adapted to cam the suture outwardly of the notches in further movement of the point into the slot, the hook being adapted to snag the suture as it is cammed out of the notches and to drag the suture through the pierced tissue as the holder and needle return to their retracted positions, the outer ends of the notches being disposed in advance of the inner ends thereof in the direction of movement of the needle from the contracted position to the retracted position.

2. A surgical stitching instrument comprising:
   A. a suture holder having a needle receiving slot and aligned notches on opposite sides of the slot adapted to receive a suture therein disposed transversely of the slot;
   B. a needle having a sharpened point, an inner edge, an outer edge divergent from the inner edge away from the point, and a hook in the outer edge spaced from the point; and
   C. means mounting the holder and needle for relative movement between a retracted position spaced to receive a tissue to be stitched therebetween and a contracted position with the point of the needle in the slot of the holder, the needle being adapted to pierce the tissue disposed therebetween as the needle moves from its retracted position toward the holder, the point being adapted to slide under such a suture in the notches of the holder in movement into the slot, the outer edge being adapted to cam the suture outwardly of the notches in further movement of the point into the slot, the hook being adapted to snag the suture as it is cammed out of the notches and to drag the suture through the pierced tissue as the holder and needle return to their retracted position in which the notches are disposed in a common plane and each has an outer open end and an inner closed end, the outer ends being disposed in advance of the inner ends in the direction of movement of the needle from the contracted position to the retracted position to facilitate the dragging of the suture therefrom and each notch is defined by a pair of legs on opposite sides thereof, one thereof being spaced from the other in the direction the suture is drawn from the notches and being shorter than said other leg.

3. A surgical stitching instrument comprising:
   A. a suture holder having a needle receiving slot and aligned notches on opposite sides of the slot adapted to receive a suture therein disposed transversely of the slot;
   B. a needle having a sharpened point, an inner edge, an outer edge divergent from the inner edge away from the point, and a hook in the outer edge spaced from the point; and
   C. means mounting the holder and needle for relative pivotal movement about a common axis between retracted positions spaced to receive a tissue to be stitched therebetween and contracted positions with the point of the needle in the slot of the holder, the needle being adapted to pierce the tissue disposed therebetween as the needle moves from its retracted position toward the holder, the point being adapted to slide under such a suture in the notches of the holder in movement into the slot of the holder, the outer edge being adapted to cam the suture outwardly of the notches in further movement of the point into the slot of the holder, the hook being adapted to snag the suture as it is cammed out of the notches and to drag the suture through the pierced tissue as the holder and needle return to their retracted positions, the hook having an outer slot providing an inner end and being extended inwardly and forwardly extended obliquely to a radius from the axis extended therethrough and an inner slot continuous with an inner end of the outer slot extended substantially tangentially of the axis from said inner end, being adapted to receive the suture therein, in substantially right angular relation to the outer slot.

4. The instrument of claim 3 in which the notches are disposed in a common plane and each has an outer open end and an inner closed end, the outer ends being disposed in advance of the inner ends in the direction of movement of the needle from the contracted position to the retracted position to facilitate the dragging of the suture therefrom and each notch is defined by a pair of legs on opposite sides thereof, one thereof being spaced from the other in the direction the suture is drawn from the notches and being shorter than said other leg.

5. A surgical stitching instrument comprising:
   A. a suture holder having a needle receiving slot and aligned notches on opposite sides of the slot adapted to receive a suture therein disposed transversely of the slot;
   B. a needle having a sharpened point, an inner edge, an outer edge divergent from the inner edge away from the point, and a hook in the outer edge spaced from the point; and
   C. means mounting the holder and needle for relative pivotal movement about a common axis between retracted positions spaced to receive a tissue to be stitched therebetween and contracted positions with the point of the needle in the slot of the holder, the needle being adapted to pierce the tissue disposed therebetween as the needle moves from its retracted position toward the holder, the point being adapted to slide under such a suture in the notches of the holder in movement into the slot of the holder, the outer edge being adapted to cam the suture outwardly of the notches in further movement of the point into the slot of the holder, the hook being adapted to snag the suture as it is cammed out of the notches and to drag the suture through the pierced tissue as the holder and needle return to their retracted positions, the hook having an outer slot providing an inner end and being extended inwardly and forwardly obliquely to a radius therethrough from the axis and an inner slot continuous with an inner end of the outer slot forwardly extended substantially tangentially of the axis from said inner end, being adapted to receive the suture therein, the outer slot being defined in part by a surface facing in the direction of retraction of the needle engageable by the suture when the suture is tensioned in the direction of such retraction of the needle upon movement of the needle relative to the tissue in the direction of its retraction, and the outer slot being defined in part by a surface facing in the direction of contraction of the needle engageable by the suture to tension the suture in the direction of the contraction of the needle upon movement of the needle relative to the tissue in the direction of its contraction, and the inner slot being defined in part by a surface facing outwardly radially of the axis engageable by the suture to tension the suture radially outwardly of the axis upon movement of the needle radially outwardly relative to the tissue, and the inner slot being defined in part by a surface facing inwardly of the axis engageable by the suture to tension the suture radially inwardly of the axis upon movement of the needle radially inwardly relative to the tissue.

6. The instrument of claim 5 in which the notches are disposed in a common plane and each has an outer open end and an inner closed end, the outer ends being disposed in advance of the inner ends in the direction of movement of the needle from the contracted position to the retracted position to facilitate the dragging of the suture therefrom and each notch is defined by a pair of legs on opposite sides thereof, one thereof being spaced from the other in the direction the suture is drawn from the notches and being shorter than said other leg.

7. A surgical stitching instrument comprising:
   A. a suture holder having a needle receiving slot and aligned notches on opposite sides of the slot adapted to receive a suture therein disposed transversely of the slot;
   B. a needle having a sharpened point, an inner edge, an outer edge divergent from the inner edge away from the point, and a hook in the outer edge spaced from the point; and
   C. means mounting the holder and needle for relative movement between retracted positions spaced to receive a tissue to be stitched therebetween and contracted positions with the point of the needle in the slot of the holder, the needle being adapted to pierce the tissue disposed therebetween as the needle moves from its retracted position toward the holder, the point being adapted to slide under such a suture in the notches of the holder in movement into the slot, the outer edge being adapted to cam the suture outwardly of the notches in further movement of the point into the slot, the hook being adapted to snag the suture as it is cammed out of the notches and to drag the suture through the pierced tissue as the holder and needle return to their retracted positions, each notch being defined by a pair of legs on opposite sides thereof, one thereof being spaced from the other in the direction the suture is drawn from the notches and being shorter than said other leg.

8. The instrument of claim 7 in which the notches are disposed in a common plane and each has an outer open end and an inner closed end, the outer ends being disposed in advance of the inner ends in the direction of movement of the needle from the contracted position to the retracted position to facilitate the dragging of the suture therefrom.

9. A surgical stitching instrument comprising:
   A. a suture holder having a needle receiving slot and aligned notches on opposite sides of the slot adapted to receive a suture therein disposed transversely of the slot;
   B. a needle having a sharpened point, an inner edge, an outer edge divergent from the inner edge away from the point, and a hook in the outer edge spaced from the point; and
   C. a forceps having a pair of pivotally interconnected arms mounting the holder and needle for movement between relatively retracted positions spaced to receive a tissue to be stitched therebetween and relatively contracted positions with the point of the needle in the slot of the holder, the needle being adapted to pierce the tissue disposed therebetween as the needle moves from its retracted position toward the holder, the point being spaced from the pivotal interconnection of the arms a radial distance slightly less than the radial spacing of the aligned notches from said pivotal interconnection and adapted to slide under such a suture in the notches of the holder in movement into the slot, the outer edge being spaced from the pivotal interconnection of the arms a radial distance slightly greater than the radial spacing of the aligned notches from said pivotal interconnection and adapted to cam the suture outwardly of the notches in further movement of the point into the slot, the hook being adapted to snag the suture as it is cammed out of the notches and to drag the suture through the pierced tissue as the holder and needle return to their retracted position in which the notches are disposed in a common plane and each has an outer open end and an inner closed end, the outer ends being disposed in advance of the inner ends in the direction of movement of the needle from the contracted position to the retracted position to facilitate the dragging of the suture therefrom and each notch is defined by a pair of legs on opposite sides thereof, one thereof being spaced from the other in the direction the suture is drawn from the notches and being shorter than said other leg.

* * * * *